(12) United States Patent
Angelides

(10) Patent No.: US 7,935,307 B2
(45) Date of Patent: May 3, 2011

(54) DISPOSABLE, REFILLABLE GLUCOMETER WITH CELL PHONE INTERFACE FOR TRANSMISSION OF RESULTS

(75) Inventor: Kimon Angelides, Houston, TX (US)

(73) Assignee: EOS Health, DVC., Houston, TX (US)

( * ) Notice: Subject to any disclaimer, the term of this patent is extended or adjusted under 35 U.S.C. 154(b) by 361 days.

(21) Appl. No.: 12/130,360

(22) Filed: May 30, 2008

(65) Prior Publication Data

US 2008/0299009 A1 Dec. 4, 2008

Related U.S. Application Data

(60) Provisional application No. 60/932,475, filed on May 31, 2007.

(51) Int. Cl.
*G01N 27/00* (2006.01)
*A61B 5/00* (2006.01)
*B65D 81/00* (2006.01)
*C12M 1/34* (2006.01)

(52) U.S. Cl. ............... 422/82.01; 600/583; 600/584; 600/300; 600/365; 422/401; 422/402; 422/55; 422/58

(58) Field of Classification Search ............ None
See application file for complete search history.

(56) References Cited

U.S. PATENT DOCUMENTS

| 7,181,350 | B2 * | 2/2007 | Oberding et al. | 702/62 |
| 2005/0169810 | A1 * | 8/2005 | Hagen et al. | 422/102 |
| 2005/0277164 | A1 * | 12/2005 | Drucker et al. | 435/14 |
| 2006/0182656 | A1 * | 8/2006 | Funke et al. | 422/58 |
| 2007/0293790 | A1 * | 12/2007 | Bainczyk et al. | 600/583 |
| 2008/0167578 | A1 * | 7/2008 | Bryer et al. | 600/583 |
| 2008/0217354 | A1 * | 9/2008 | Newman et al. | 221/229 |

* cited by examiner

*Primary Examiner* — Joseph W. Drodge
*Assistant Examiner* — Jennifer Wecker
(74) *Attorney, Agent, or Firm* — Eric P. Mirabel

(57) ABSTRACT

A disposable glucometer is disclosed which includes a testing region for receiving a test strip and electronic components to perform blood glucose monitoring, a cell phone interface for relaying test results to a monitoring station or server (which can be through a Bluetooth radio), and a multi-strip test strip holder. The glucometer includes a mechanism to automatically load test strips, one at a time, from the multi-strip test strip holder into the testing region, and a mechanism to eject the strip from the testing region after the test is complete. The test strip holder is preferably encased in a transparent material or otherwise includes a visual indicator so that the number of strips remaining strips and available for testing can be determined. In one embodiment, the entire unit is disposable, and is discarded when all of the strips have been used. In another embodiment, the test strip holder portion of the unit is removed and replaced with a new test strip holder which is loaded with test strips.

8 Claims, 4 Drawing Sheets

DISPOSABLE, REFILLABLE GLUCOMETER WITH CELL PHONE INTERFACE FOR TRANSMISSION OF RESULTS

RELATED APPLICATIONS

This application claims priority to U.S. provisional application 60/932,475, filed May 31, 2007.

FIELD OF THE INVENTION

The invention relates to a disposable glucometer which can transmit blood glucose readings through a wireless interface.

BACKGROUND

Diabetic patients typically monitor their blood glucose levels using disposable test strips which are part of a system which senses the concentration of blood glucose electrochemically, using a battery-powered, hand-held glucometer. A typical glucometer of such design has a blood sample strip-receiving region, into which the user first inserts a disposable test strip and then applies a blood sample for analysis. A display screen on the meter displays the results of the blood glucose analysis. In all existing glucometers, the test strip are separated from the glucose sensing portion—the strips are typically stored separately in a packet or bottle.

It is preferred if the glucometer can be coupled to a data communication device, typically a wireless modem (see U.S. Pat. No. 7,181,350), so that the results of a blood glucose analysis performed and stored by the meter can be reported directly to a monitoring facility that tracks the results and the patient's status.

Conventional glucometers require the test strips to be loaded in one at a time, as each test is performed successively over time (U.S. Pat. No. 6,743,635). Through normal use, the unit may become contaminated with blood over time. Also, the separately-stored strips are subject to spoilage and contamination. Also, communication through a wireless modem requires purchase of an interface which is more expensive and cumbersome than a cellular phone. A product which avoids these shortfalls is desirable.

SUMMARY

A disposable glucometer is disclosed which includes a testing region for receiving a test strip and electronic components to perform blood glucose monitoring, a cell phone interface, and a multi-strip test strip holder. The glucometer includes a mechanism to automatically load test strips, one at a time, from the multi-strip test strip holder into the testing region, and a mechanism to eject the strip from the testing region after the test is complete. The test strip holder is preferably encased in a transparent material or otherwise includes a visual indicator so that the number of strips remaining strips and available for testing can be determined. In one embodiment, the entire unit is disposable, and is discarded when all of the strips have been used. In another embodiment, the test strip holder portion of the unit is removed and replaced with a new test strip holder which is loaded with test strips.

The unit also may include a cell phone connection, including a connection through a Bluetooth radio, so that the results can be loaded directly to a cell phone and transmitted to a monitoring station or a server which stores the results, where they can be evaluated and feedback on diet, drug dosing, or exercise can be transmitted back to the user. The features and operation are described further below.

DETAILED DESCRIPTION

Figure 1:
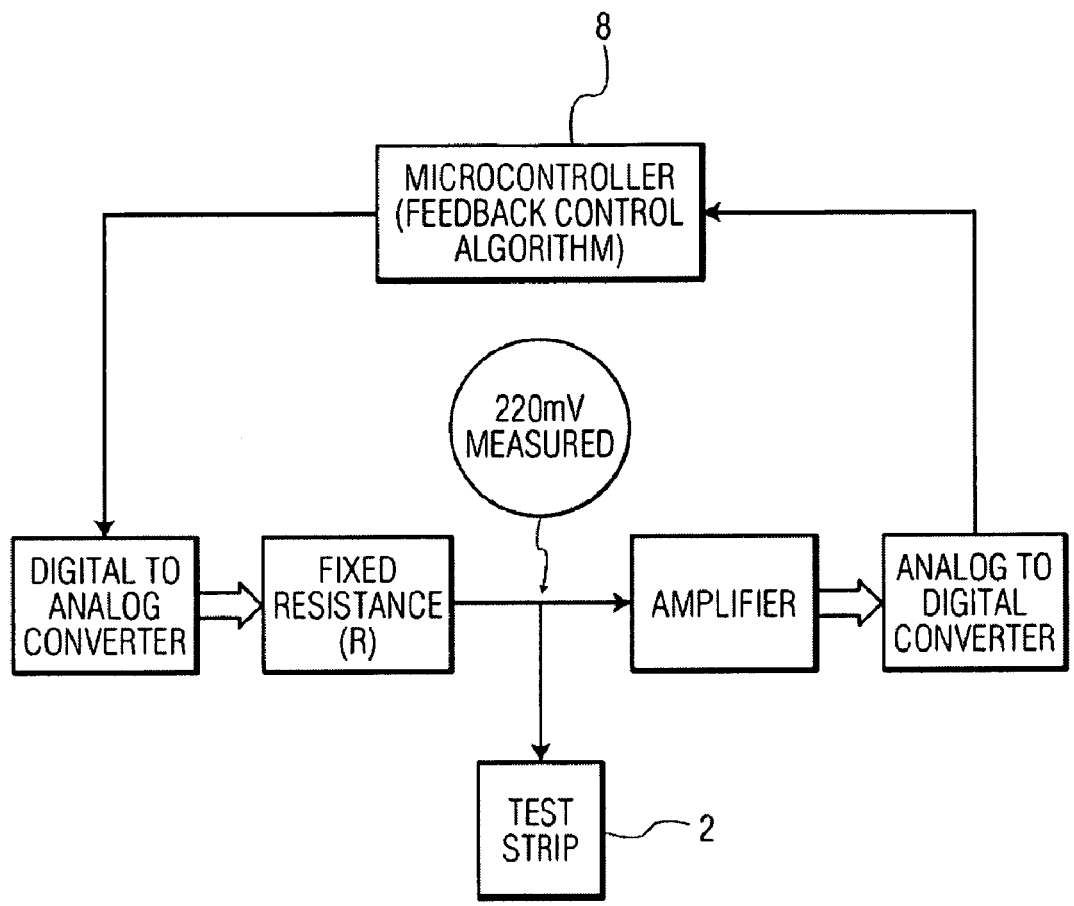
FIG. 1 is a block diagram showing how a glucometer, as disclosed herein, samples blood glucose readings.

A block diagram of the operation of an embodiment of the disposable glucometer disclosed herein is 5110$wn$ in FIG. 1. Preferably, the glucometer is continuously powered and is continuously monitoring activity. Upon loading of a blood glucose test strip 2, it commences a blood glucose reading. This glucometer embodiment does not measure the current directly—though other glucometers could be used which do measure the current directly and which are also disposable (like the one disclosed herein).

Using existing glucose monitoring strips, the glucometer of FIG. 1 requires 220 millivolts maintained across two electrodes. One of the electrodes is a reference electrode and the other is the working electrode. The reference electrode is connected to electrical ground (common), and the working electrode is maintained at 220 mV. A microprocessor controlled voltage source (e.g., a Digital to Analog Converter—DAC), produces a voltage which is connected to the working electrode through a resistor of known value. A volt meter (e.g., an Analog to Digital Converter—ADC) is also connected to the working electrode to ensure that the 220 mV is always maintained.

When a blood sample is placed on the test strip, the resistance of the strip immediately drops causing current flow. This causes the voltage on the working electrode to drop, which is sensed by the ADC and is immediately compensated for by the DAC. Over the next 10 seconds the resistance of the strip will first decrease for about 9 seconds, and thereafter, will increase causing the current flow to decrease. The ADC continuously monitors this change and signals the DAC to adjust the output voltage to maintain 220 mV on the working electrode.

During seconds 9 through 10, the calculated current values are averaged and this average is used to derive the actual blood glucose value. Because the voltage produced by the DAC is always known, the series resistance is known, and the working electrode voltage of 220 mV is known, the current through the strip can be accurately calculated. The blood glucose value is a direct function of the current flowing through the test strip and is adjusted for the ambient temperature during the test, and the strip manufacturing lot variance.

Figure 2A:
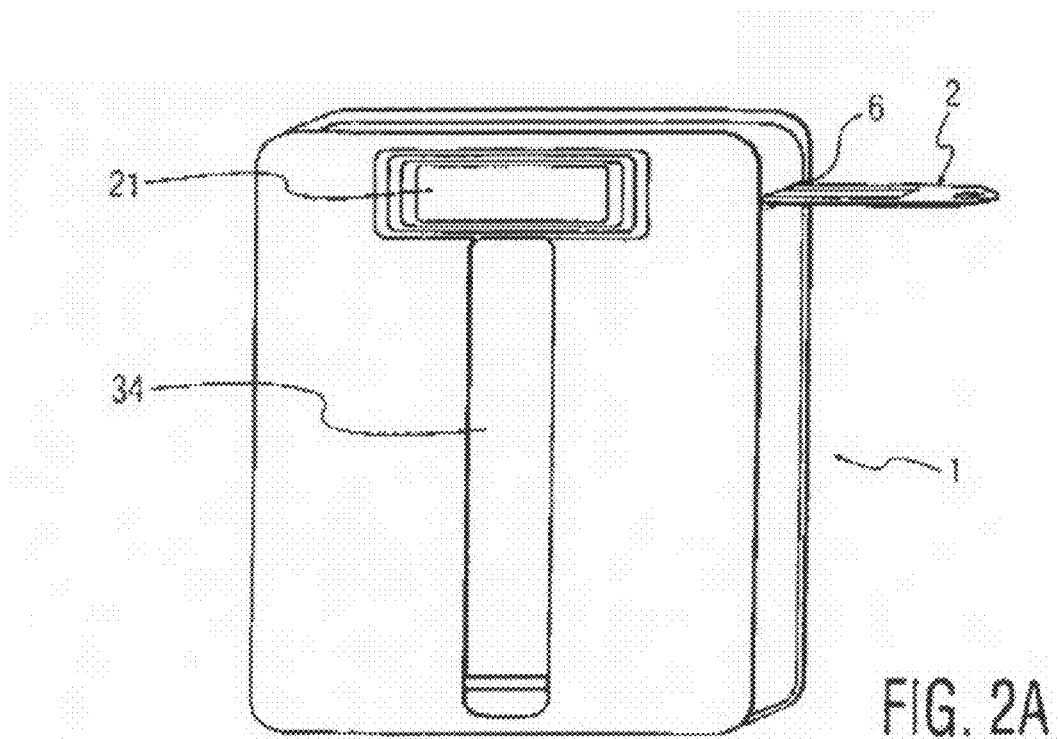
FIG. 2A is an elevated view of a disposable glucometer with a strip in place.
Figure 2B:
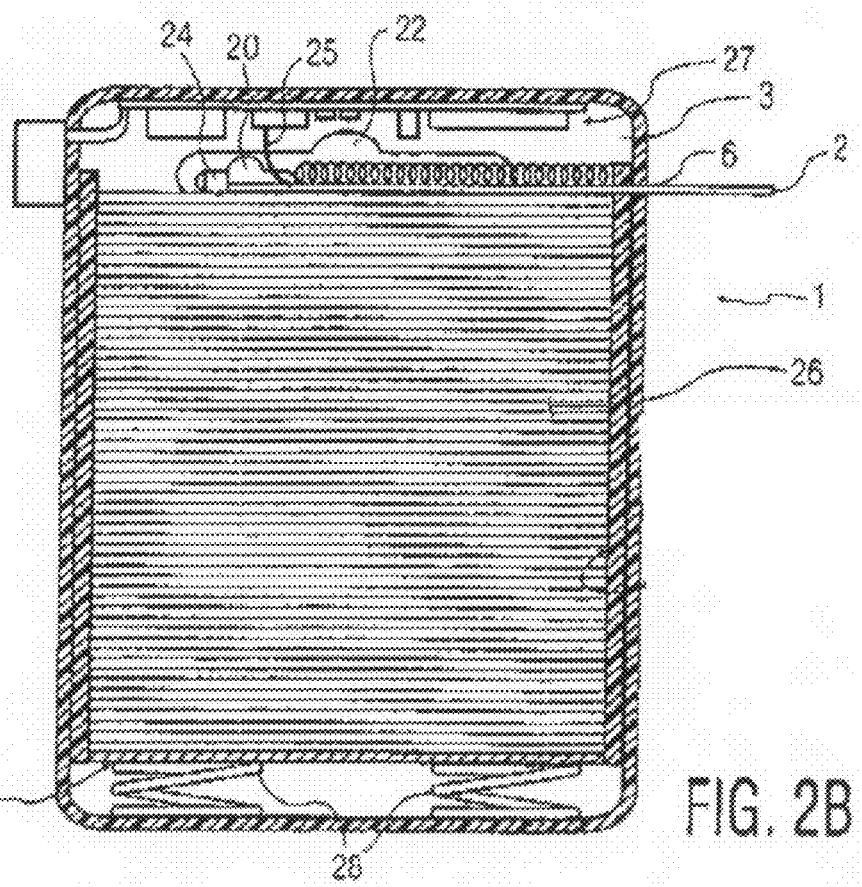
FIG. 2B is a sectional view of the device shown in FIG. 2A.
Figure 2C:
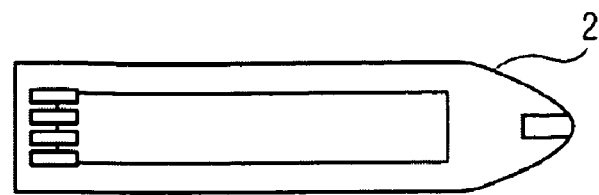
FIG. 2C is a plan view of a glucose strip for use in the glucometer of FIGS. 2A and 2B.
Figure 2D:
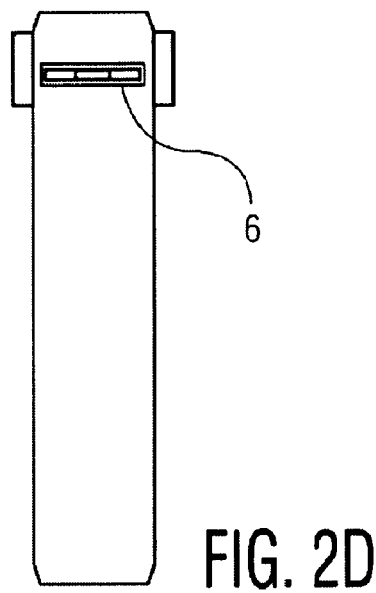
FIG. 2D is an elevated view of the side of the glucometer of FIGS. 2A and 2B which receives the glucose strip.
Figure 2E:
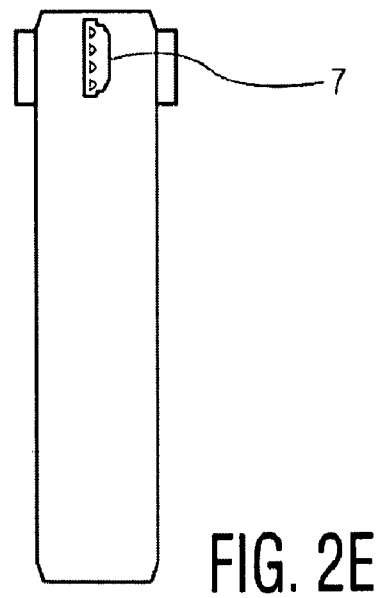
FIG. 2E is an elevated view of the opposite side of the glucometer from that in FIG. 2D.

Referring to the device 1 in FIGS. 2A-2E, a Test Strip 2 is loaded into the Test Strip chamber 3, and advanced (by operator pressure on tab 21) until slider cam 20 settles into the receiving port 22. In this position, strip 2 extends partially out of the port 6 (as in FIG. 3), and a blood sample is applied to the exposed portion of strip 2. The Microcontroller 8 of FIG. 1 (as electronically linked to strip 2 through Strip Mating Connector 25 to Glucometer Electronics 27 in the upper part of chamber 3, as shown in FIG. 2B) recognizes the loading of the strip, and the Glucometer Electronics 27 performs the glucose strip reading function as depicted in FIG. 1:

1. Exactly 200 mV potential is produced across the working and reference electrodes of the strip.
2. When blood is applied to the strip, current begins to flow into the strip.
3. After 9 seconds an average of the current is calculated continuously until 10 seconds is reached.
4. The average current value directly correlates to the blood glucose level.
5. This value is further compensated for temperature variations and test strip production lot variations.

The microcontroller 8 then executes the steps described above to accurately read the current flowing into the test strip. Over time, the resistance of the test strip continues to increase requiring the DAC to decrease its output. Because the voltage output of the DAC is known the fixed resistance is known, and the 220 mV reference is known, the current flowing into the test strip can be derived as:

$$I_{strip} = (V_{DAC} - V_{ref})/R$$

This measurement technique provides a very accurate high resolution current value with low noise, high repeatability, and a very wide dynamic current range without additional support electronics.

Once the Microcontroller 8 of FIG. 1 has confirmed that the blood sample has been acquired, the following occurs:

1. The digital representation of the Test Strip 2 current is sampled and stored at regular intervals over a fixed period of time.
2. The slope of the current is noted. If the slope is trending in the wrong direction, the test is aborted with an error.
3. A temperature value (from a sensor) is acquired by the Microcontroller 8 at regular intervals and is averaged over the test time.
4. A signal can be sent to a Bluetooth radio (and in turn to a cellular phone or PDA) indicating that a test is in progress. The Bluetooth radio in turn, relays this information to the cellular phone. The Bluetooth radio may not be included with the disposable glucometer, and instead, a cell phone connector, which allows test data to be transmitted from the glucometer to a phone or PDA, may be substituted.

At the completion of the test, the blood glucose value is determined as a function of the following:

1. The slope of the digital representation of the Test Strip 2 sampled current verses time.
2. The average temperature during the test.
3. The test strip lot calibration value which is used to access a library stored within the Microcontroller 8 to compensate the calculated blood glucose value.
4. An indicator such as an LED first indicates a test in progress, then turns off to indicate that the test is completed and that it is now safe to remove the test strip. The blood glucose value is shown on the LCD display.

The final determined blood glucose value is then evaluated by the Microcontroller 8 to ascertain it is within an expected range or if the blood sample was actually a standard solution for test and verification. The results of the test are then sent to the Bluetooth Radio (not shown) which in turn, relays this information to a Cellular Phone or PDA (or test results are sent directly to the Cellular Phone, if it is linked with a cable through connector 7, as in FIG. 2E) for storage and display. If the Cellular phone/Bluetooth link is not available, then the time of the blood glucose reading and the value of the reading are stored in the non-volatile memory of the glucometer. When the cellular phone becomes available, the readings are then transferred to its memory. The Microcontroller 8 then enters into a low power sleep state and does not awaken until a new test strip is inserted.

FIGS. 2A-2E and 3 show a disposable glucometer 1 and a test strip 2, where the unit includes the optional cell phone connector 7 on one side. A test strip 2 is uploaded and advanced from holder 26 by gripping tab 21 on the outer surface of glucometer 1, and pushing it forward to slide along travel bore 32, to first stop point (where the slider cam 20 settles into the receiving port 22). This action causes the strip catch bar 24 to contact the rear edge of the uppermost strip 2 in the holder 26 (where the layers of strips 2 are pressed towards the strip catch bar 24 under the action of the lowermost springs 28) and advance the caught strip 2 through the test strip port 6, to expose a portion of its upper surface, in preparation for application of a test sample.

To perform a test, a blood sample is placed on the exposed portion of the strip 2, and the electronic test described above and shown in FIG. 1 is performed. Once the cell phone (not shown) indicates that the test is complete, the unit can be disconnected from the cell phone (or the Bluetooth can be turned off, as applicable). The tab 21 is now be pushed down (to disengage slider cam 20 from the receiving port 22) and forward further, until slider cam 20 reaches the end of the travel bore 32, causing the used test strip 2 to be ejected. A window 34 on the side of the glucometer 10 allows visual determination of the number of remaining test strips 2.

Figure 3:
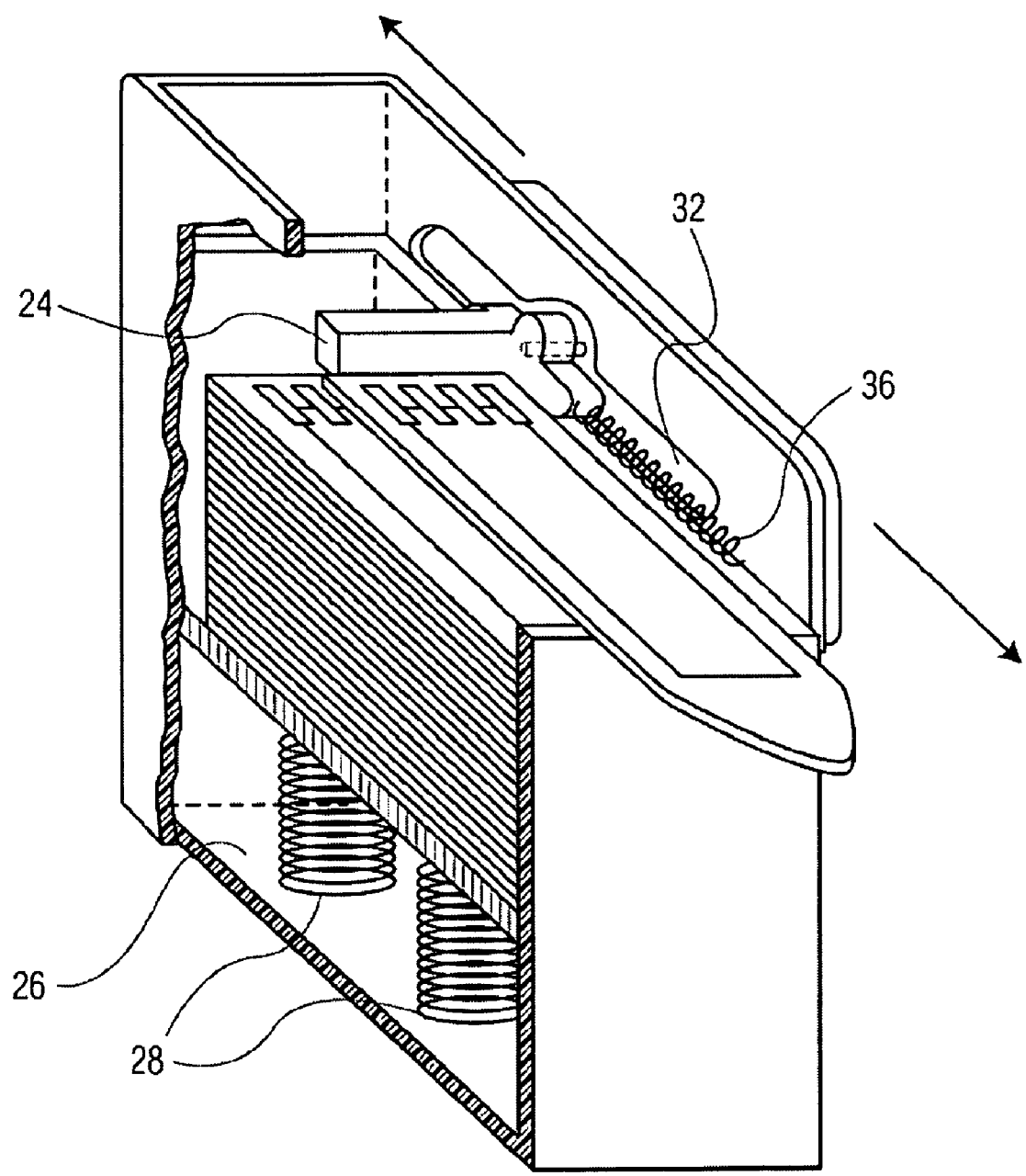
FIG. 3 is a cut-away view showing the functional portions of the glucometer shown in FIGS. 2A-2E.

Referring to FIGS. 2B and 3, where the working parts of the glucometer can be seen, a test is carried out once a test strip 2 has been partially exposed externally (in the position shown in FIG. 3) provided the glucometer is in communication with a cell phone. When the tab 21 is pushed forward to where slider cam 20 settles into the receiving port 22, and strip catch bar 24 has contacted and advanced the uppermost strip 2, that test strip 2 will be positioned beneath the Strip Mating Connector 25, creating electrical contact between the test strip 2 and the Glucometer Electronics 27. Following application of a sample and completion of a glucose blood test, the glucometer is disconnected from the Cell phone (or the Bluetooth radio is turned off).

Advancing the tab 21 to the end of travel bore 32 (by pushing it downward and forward to disengage the slider cam 20 from the receiving port 22) allows the used test strip 2 to be pushed out of contact with the Strip Mating Connector 25, and to eject the test strip. A spring 36 resisting the forward motion of the slider cam 20 forces the slider cam 20 to return to its home position, where it can engage another test strip. The Strip Advance Platform 30 and Springs 28 push the uppermost test strip 2 into position to be engaged and advanced by slider cam 20. The Window 34 on the side of the glucometer allows viewing the Strip Advance Platform 38 to provide a visual indication of the number of remaining strips (based on the platforms relative location with respect to the uppermost portion of the Window 34). When all of the test strips have been depleted, the glucometer can be discarded, or, only the inner portion with the chamber 26 can be discarded, and replaced with a new chamber 26 filled with test strips. Where only the chamber 26 is discarded, all other portions of the unit are retained. Where a Bluetooth radio is part of the unit, due to the expense of a Bluetooth radio, it is preferable to have only the chamber 26 as a disposable portion.

It should be understood that the embodiments, examples, and the terms and expressions herein are exemplary only, and not limiting, and the scope of the invention is defined only in the claims which follow and includes all equivalents of the subject matter of those claims.

What is claimed is:

1. A glucometer holding multiple glucose test strips which can be loaded for testing in succession, and each used test strip can be ejected following test completion, comprising:

a body outlining a chamber holding multiple glucose test strips, said chamber including a platform with glucose test strips placed thereon in a stack on one side of the platform, and springs positioned on the other side of the platform so as to advance the glucose test strips in the direction of the stack;

a cam with an edge portion designed to fit behind the test strip in the stack which is furthest from the platform to allow its selection from the other test strips in the stack, wherein the cam and an edge portion reside in a slot in the body such that the cam can move in a direction transverse to the direction of the stack and then stop at a particular location so that the selected test strip extends a predetermined amount through a port in the side of the glucometer, such that a sample can be applied to the exposed portion of said selected test strip for testing, when said selected test strip is in such testing position;

electronic testing components in electrical connection with the selected test strip when it is said testing position, wherein said electronic testing components include a microcontroller which identifies when the selected test strip is at the testing position and initiates testing for glucose in a sample in contact with said selected test strip:

a wire or wireless link for connecting the glucometer to a wireless device which can transmit test results to a monitoring station; and said cam and said bore are designed such that the cam can further advance the selected test strip following testing, such that, said selected test strip is ejected through the port and from the glucometer, after which, the cam returns to a position where it can advance the next test strip in the stack.

2. The glucometer of claim 1 wherein the chamber is detachable and can be replaced with a different test strip holder filled with unused test strips.

3. The glucometer of claim 1 wherein the number of test strips in the holder can be viewed.

4. The glucometer of claim 1 wherein the cam and said bore are designed such that the cam's forward travel terminates at the end of the bore whereby the strip is ejected.

5. The glucometer of claim 1 wherein the electronic testing components maintain a consistent reference voltage across the strip and determine the variation in current flowing through the strip, over time, to determine the glucose in the sample.

6. The glucometer of claim 1 wherein the wireless device is a Bluetooth radio, cellular phone or PDA.

7. The glucometer of claim 6 wherein glucometer is direct is connected to a cellular phone or PDA.

8. The glucometer of claim 6 wherein test results are transmitted from the cell phone or PDA to a monitoring station or a server which stores the results.

\* \* \* \* \*